US008013121B2

(12) United States Patent
Xiong et al.

(10) Patent No.: US 8,013,121 B2
(45) Date of Patent: Sep. 6, 2011

(54) ISOLATED NATURE-IDENTICAL COLLAGEN

(75) Inventors: Xin Xiong, Stuttgart (DE); Heike Mertsching, Sindelfingen (DE); Steffen Rupp, Stuttgart (DE); Herwig Brunner, Weilheim (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 197 days.

(21) Appl. No.: 12/302,667

(22) PCT Filed: May 30, 2007

(86) PCT No.: PCT/EP2007/004767
§ 371 (c)(1),
(2), (4) Date: Nov. 26, 2008

(87) PCT Pub. No.: WO2007/137827
PCT Pub. Date: Dec. 6, 2007

(65) Prior Publication Data
US 2010/0216239 A1    Aug. 26, 2010

(30) Foreign Application Priority Data

May 31, 2006   (DE) .......................... 10 2006 026 591

(51) Int. Cl.
*C07K 1/14* (2006.01)
(52) U.S. Cl. ....................................................... 530/356
(58) Field of Classification Search ........................ None
See application file for complete search history.

(56) References Cited

FOREIGN PATENT DOCUMENTS

| DE | 24 62 222 | 5/1976 |
| DE | 100 62 623 | 12/2001 |

OTHER PUBLICATIONS

English machine translation of Japanese Patent JP 409031100—published Feb. 4, 1997 (Kato et al.).*
USPTO Certified Translation of Japanese Patent JP 409031100—published Feb. 4, 1997 (Kato et al.).*
Fessler et al., J. Supramolecular Structure, 1974, vol. 2, pp. 103-107.*
Zimmerman et al. Eur. J. Biochem. 1970, vol. 16, pp. 217-225.*
Piez et al., "The Chromatographic Separation and Amino Acid Composition of the Subunits of Several Collagens", Biochemistry, 1963, 2(1):58-66.*
Definition "Culture Medium", from FreeDictionary on-line, <www.thefreedictionary.com>.*
M. Stoltz, et al., "Non-Helical Regions in Rat Collagen α 1-Chain," FEBS Letters, vol. 26, No. 1, (1972), pp. 61-65.
U. Becker, et al., "$NH_2$-Terminal Extensions on Skin Collagen from Sheep with a Genetic Defect in Conversion of Procollagen into Collagen," Biochemistry, vol. 15, No. 13, (1976), pp. 2853-2862.
U. Becker, et al., "Carboxyterminal Antigenic Determinants of Collagen from Calf Skin Localization Within Discrete Regions of the Nonhelical Sequence," European Journal of Biochemistry, vol. 28, No. 2, (1972), pp. 221-231.
B.C. Adelmann, "The Structural Basis of Cell-Mediated Immunological Reactions of Collagen Reactions of Collagen, Reactivity of Separated α-Chains of Calf and Rat Collagen in Cutaneous Delayed Hypersensitivity Reactions," Immunology, vol. 23, No. 5, (1972), pp. 739-748.
Roche Lexikon Medizin, 4.Auflage; Urban & Fischer Verlag, Munchen, (1999), pp. 1-2.

* cited by examiner

*Primary Examiner* — Suzanne M. Noakes
(74) *Attorney, Agent, or Firm* — Dickstein Shapiro LLP

(57) ABSTRACT

The present invention concerns isolated collagen, the method for its production, and isolation of the collagen from collagen-containing tissues, as well as the use of the isolated collagen in a biomatrix as an in vitro test system, tissue replacement or organ replacement.

15 Claims, 1 Drawing Sheet

ISOLATED NATURE-IDENTICAL COLLAGEN

DESCRIPTION

Figure 1:
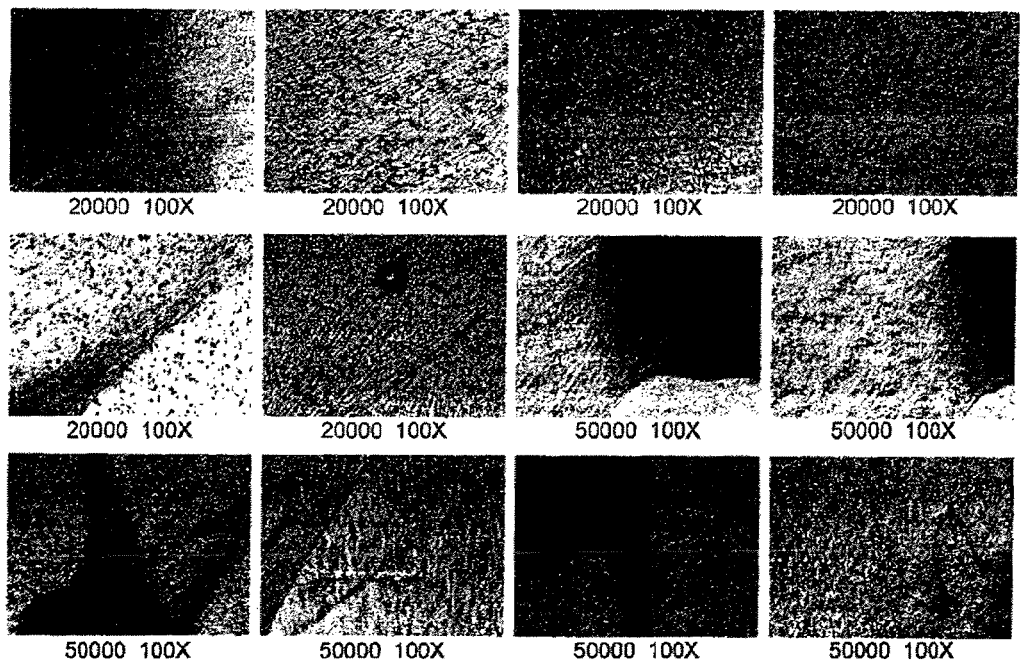

The present invention concerns isolated collagen, a method for the production and isolation of collagen from collagen-containing tissue, and the use of the isolated collagen in a biomatrix as an in vitro test system, tissue replacement or organ replacement.

PRIOR ART

Extracellular matrices (ECM) or support structures for culturing cells, so-called biomatrices, are usually produced from isolated collagen, i.e., from matrix protein isolated from collagen-containing tissue. Such biomatrices play an important role, particularly in regenerative medicine. Here, the purpose of tissue engineering is to assist or replace diseased, failed, or lost tissue or organ functions. For this purpose, one generally cultures ex vivo tissue or organ structures by inoculating prepared support structures or biomatrices with at least one tissue-specific cell type, followed by culturing. The biomatrix and the cells cultured on it form the tissue or organ equivalent or replacement.

For the realization of tissue-specific functions, it is necessary for the cells that are applied to the biomatrix to reorganize, or form de novo, the matrix proteins. For the successful culturing of cells on such support structures, it is therefore important that the matrix proteins present have properties that are, if possible, native or nature-identical.

Known biomatrices are usually prepared from collagen that is isolated from freshly prepared, collagen-containing tissues extracted from, for example, skin or tendons.

A known extraction method is extraction with aqueous acetic acid. In the usual extraction protocols, the acetic acid is used at a concentration of 0.1% up to 500 mmol/L. For the extraction of collagen from collagen-containing tissues, for example, rat tail tendons (RTT), the tissue is stirred with acetic acid over a time period from 20 h to 7 days, usually at room temperature. The primary disadvantage is that the native structure of the extracted matrix proteins is attacked during the incubation due to the acidic hydrolysis by the acetic acid and the enzymatic digestion by the proteinases usually present, and the matrix proteins are partially or completely denatured in the process. The subsequent regeneration of the original native collagen structure and the reconstitution of the biological functions of the matrix proteins are therefore limited. If the matrix proteins that have been isolated by acetic acid extraction and partially denatured are then lyophilized in addition, the properties of the collagen product reconstituted using the lyophilizate deviate considerably from native collagen, so that its use for culturing tissue-specific cells is greatly restricted. Moreover, the matrix proteins that have been isolated by means of the acetic acid extraction present additional disadvantages, like uncontrolled (usually one-dimensional, vertical) shrinkage.

The use of such biomatrices produced in a known way is very limited in in vitro test systems, for example, to test new active ingredients, because the cultured cells, due to the denatured matrix proteins present, often develop unfavorable changes of their physiological and morphological properties and cell functions, compared to in vivo or in situ conditions. Consequently, the transferability of in vitro test results becomes more difficult.

There is a need for alternative and improved means and methods for the simple obtention of improved, i.e., largely nature-identical, isolated collagen, and biomatrices prepared therefrom that do not present the disadvantages of the prior art.

Problem Formulation

The technical problem that is the basis of the present invention primarily consists in producing a method and means for the production, obtention or isolation of collagen or matrix proteins from collagen-containing tissues, in which the isolated collagen presents a large portion of matrix proteins with nature-identical structure. An additional related problem consists in producing improved biomatrices, which are suitable for the production of organ or tissue replacement or equivalents, or in vitro test systems. An additional related technical problem consists in producing in vitro test systems for the analysis and diagnosis of infections, as well as for the examination and testing of degenerated or genetically altered human or animal cells, diagnostic and therapeutic products that overcome the above-mentioned disadvantages of the prior art.

The underlying technical problem is essentially solved by a method for isolating collagen or collagen matrix proteins from collagen-containing tissues according to the characteristics of claim 1.

According to the invention, in a step (a) collagen-containing fibers are isolated from the collagen-containing tissue, and in a subsequent step (b) the isolated collagen-containing fibers are incubated in an aqueous urea solution that contains urea at a concentration of 5-15 mol/L, particularly 7-12 mol/L, particularly preferably approximately 9 mol/L, in which or in whereby a collagen-containing fraction is released and dissolved from the fibers. According to the invention, the next step (c) consists of separating the dissolved collagen-containing fraction of fibers and tissue residues so that an aqueous collagen-containing solution is obtained. Advantageously, in an additional step (d) the urea is dissolved from the collagen-containing fraction, and it is preferred that, in an additional step (e) the fraction from which the collagen-containing urea has been removed is preferably renatured in a buffer solution, so that renatured isolated collagen is obtained in an aqueous solution.

Thus, according to the invention, isolated collagen-containing fibers are essentially incubated with a highly concentrated urea solution for a certain time period, in which the collagen matrix proteins are dissolved out of the tissue. Surprisingly, the extraction according to the invention allows the isolation of predominantly nature-identical matrix proteins, which can be nearly completely renatured after the separation of the urea in an aqueous buffer solution. Circular dichroism spectroscopy (CD) of the collagen fraction isolated according to the invention reveals the typical "triple helices" structure of native collagen, which is particularly characterized in the CD spectrogram by a negative band between 217 and 227 nm and optionally a weaker negative band close to 200 nm. UV spectroscopic examination (UV) of the collagen fraction isolated according to the invention also presents a characteristic amino acid signature of histidine at 213 nm, which also indicates an intact native protein structure. Consequently, here UV is advantageously suitable for a simple quantification of the collagen matrix proteins without requiring the use of antibody tests, which are known to be disadvantageous, since they frequently present the disadvantage of cross reactions. Therefore, another object of the invention is a method for isolating collagen or collagen matrix proteins, in which the collagen concentration determination is made by UV.

The collagen isolated according to the invention can be advantageously used to obtain a biomatrix, and from it a tissue or organ replacement or equivalent, or an in vitro test system that no longer presents the particular disadvantage of one-dimensional shrinkage. The proliferation of tissue-specific cells and the de novo synthesis of matrix by cells from the biomatrix occurs with improvement or at least in the same measure as with the biomatrices obtainable with known methods.

In a preferred embodiment of the method, the collagen-containing tissue used, from which the collagen-containing fibers are isolated in step (a), consists of rat tail tendons isolated from rat tails. In an alternate variant, the collagen-containing tissue is a preferably acellularized porcine small intestine.

It is preferred in step (b) to stir the urea solution with the collagen-containing fibers. It is preferred in step (b) to incubate the collagen-containing fibers with the urea solution for 12-36 h, particularly preferably for approximately 24 h, preferably under stirring, so that the collagen-containing fraction is particularly effectively dissolved out of the fibers.

In step (c), the dissolved collagen-containing fraction is preferably dissolved from fiber and tissue residues by mechanical separation methods in a way which is known in itself, preferably by centrifugation. In another preferred variant, the separation is carried out alternatively or additionally by filtration.

For certain application fields, it is advantageous in step (c) for the dissolved collagen-containing fraction to be separated by fractionation using gel filtration, and optionally split. Optionally, several of the dissolved collagen fractions can then be recombined. In this way, the person skilled in the art can chose the advantageous and/or tissue-specific composition of the matrix protein.

It is preferred to subject the isolated collagen-containing fraction or the collagen fractions separated by fractionation to analytical procedures. The characterization of the matrix proteins is preferably carried out by CD. In an additional preferred variant, the characterization alternatively or additionally occurs by UV. In an additional preferred variant, the characterization alternatively or additionally occurs by ESI-MS MS. In an additional preferred variant, the characterization alternatively or additionally occurs by MALDI-TOF TOF. The protein fractions can be dissolved and isolated in a manner known in itself by one- or two-dimensional gel electrophoresis, isoelectric focusing and/or SDS-PAGE.

To separate the urea contained in the solution from the collagen-containing fraction, it is preferred to carry out a gradient dialysis in step (d). Here it is preferred to carry out the dialysis in the colds, i.e., preferably 0° C. to approximately 10° C., preferably at approximately 4° C., and for a time period of 4-12 days, preferably 7 days. It is preferred to dialyze against water. The aqueous collagen solution so prepared preferably presents a collagen concentration ranging from approximately 3 to approximately 8 mg/L.

In a variant of the invention, the dialyzed fractions are concentrated to a certain collagen content, preferably by a factor of 2 or 3. The concentrates obtained are particularly suitable for subsequent separation by SDS-PAGE, for further characterization, as well as for the production of boil-proof biomatrices.

The collagen fraction is then preferably renatured in the additional step (e) in a phosphate buffered saline solution (PBS) or similar media or buffer systems. As a result of the renaturing, the matrix proteins essentially redevelop all the natural properties and native structural parameters, and can thus be used for the production of improved biomatrices.

An additional object of the invention is an isolated collagen, which is producible by the method according to the invention or is produced by it. The aqueous collagen solution obtainable according to the invention contains a large proportion of native collagen in an aqueous medium, particularly a proportion of the total collagen in solution of $\geq 50\%$, particularly $\geq 60\%$, $\geq 70\%$, $\geq 80\%$, $\geq 90\%$ or $\geq 95\%$, preferably $\geq 99\%$. In circular dichroism spectroscopy, such a collagen preferably presents the characteristic triple helices "signature" of the triple helices structure (see above).

In an additional preferred embodiment of the invention, the obtained collagen-containing fraction aqueous solution is lyophilized so that a storable dry collagen production is obtained. If the lyophilized collagen obtained is then mixed with water or an appropriate medium, a nearly completely native three-dimensional structure of the collagen then advantageously forms. Destruction of the naturally occurring triple helix structure by the lyophilization does not occur. An additional object of the invention is also a lyophilized collagen that can be produced according to the invention. For this purpose, the aqueous collagen fraction is lyophilized in a way that is known in itself, so that a dry, storable collagen production is obtained. Naturally it is also possible to store the solution on an intermediate basis in the frozen state, for example, at −10° C. to −80° C., preferably at approximately −20° C.

An additional object of the invention is a method for the production of a biomatrix that is characterized in that first the steps (a) to (e) of the method according to the invention are carried out, which results in an aqueous collagen solution or collagen-containing fraction, and in an additional step (f) the collagen solution obtained is mixed with cell culture medium or the like in a ratio from 2:1 to 1:2, preferably a ratio of 1:1, to obtain a collagen-containing matrix precursor solution. The collagen content of the solution is preferably 3-8 mg collagen per mL solution, more preferably 5-7 mg collagen per mL solution. In an additional step (g), the matrix precursor solution so obtained is gelled, preferably at elevated temperature, preferably at 21-37° C., to obtain a collagen-containing biomatrix. Alternatively, the collagen gel is obtained by dissolution according to the invention of obtainable lyophilized collagen productions.

An additional object of the invention is accordingly also a biomatrix that is producible by the above-mentioned method or preferably prepared by it. An additional object of the invention is also a biomatrix that contains the collagen that has been isolated by the method according to the invention, or preferably consists of it. The invention primarily concerns a preferably gel-like biomatrix for use in culturing methods, for example, to culture cells of a certain tissue type or cells of several tissue types. The combination, which is provided according to the invention, of a biomatrix and cells cultured therein can be used for the production of an in vitro tissue or organ test system.

The term in "biomatrix" denotes a gel structure that contains collagen, cell culture medium, buffer and optionally serum. Preferred culture media are DMEM (Dulbecco's Modified Eagle Medium) and M199. Hepes buffer is a preferred buffer system. As serum, it is preferred to use fetal calf serum (FCS) or human, particularly autologous, serum. In a preferred embodiment, the pH of the solution consisting of cell culture medium, buffer and serum is 7.5-8.5, for example 7.6-8.2, particularly 7.8. Depending on the application field, naturally the biomatrix can contain additional factors, for example, growth factors, proteoglycans, glucosamine glycans, adhesives, antibiotics, selection agents and other extracellular matrix components.

For the production of a cell-containing biomatrix, it is preferred to use a multiply (x-fold) concentrated cell culture medium, serum and buffer mixed with precultured cells, in which it is preferred to use $1-2\times10^5$ cells per mL, preferably $1.5\times10^5$ cells per mL. Subsequently, a mixture is prepared in the cold at 0-10° C., particularly 4° C., for example, in a ratio from 1:2 to 2:1, with the collagen solution obtainable according to the invention. The mixing ratio (volume) of collagen solution to cell suspension (buffer, serum, cell, culture medium) is preferably 1:1, in which in the case of an x-fold concentrated gel solution, a volume ratio of (x−1):1 collagen solution to gel solution is particularly preferred. Subsequently, the suspension is pipetted into culture vessels and, after gelling at increased temperature, preferably 37° C., which takes a few minutes as a rule, coated with medium (submerged culture). The biomatrix can be cultured, for example, for 2 days. Subsequently, cells of other tissue types can be established and cultured.

A preferred embodiment of the invention comprises the culturing of animal or human cells in a three-dimensional gel-like biomatrix for the multiplication of these cells and for the production of a three-dimensional animal or human in vitro tissue or organ test system. The results obtained with the tissue organ test systems according to the invention can have greater validity than results determined with animal results, and they can ensure better transferability to humans. Another object of the invention is a tissue equivalent or replacement that contains the biomatrix according to the invention, as well as vital tissue cells, particularly tissue-specific cells which are preferably cultured in and/or on the biomatrix. Another object of the invention is an organ equivalent or replacement that contains the biomatrix according to the invention, as well as vital tissue cells, particularly organ-specific cells which are preferably cultured in and/or on the biomatrix. In a particularly preferred embodiment, the invention comprises the culturing of human dermal fibroblasts in the biomatrix for the production of a dermis equivalent or an epidermis equivalent consisting of three-dimensional human in vitro skin equivalent.

The expression "culturing cells" denotes the maintenance, preferably in vitro, of the tissue-typical vital functions of cells, particularly of fibroblasts, in an appropriate environment, for example, with feeding and removal of metabolic educts and products, also particularly including multiplication of the cells. Naturally, in connection with the present invention dermal fibroblasts particularly denote fibroblasts that occur in the dermis or that have been genetically altered, or their precursors. Fibroblasts represent the precursors of dermal fibrocytes. The fibroblasts can be of animal or human origin; can be from freshly isolated tissues or primary cells or genetically altered or transformed cell lines like WI-38, NIH/3T3, MRC-5. The biomatrix contains the fibroblasts to be cultured and the collagen framework at a concentration of 2-5 mg formed de novo from the collagen solution that is producible according to the invention, preferably 3.5-4.5 mg collagen per mL biomatrix. The collagen framework is obtained from a preferably cell-free solution of collagen obtainable according to the invention, in which the protein concentration of the collagen solution is preferably 5-7 mg/mL. For the production of a, for example fibroblast-containing, biomatrix, the collagen solution is mixed at 4° C. and thoroughly blended with a cell solution or suspension that contains a preferably five-fold concentrated cell culture medium, a buffer, preferably Hepes buffer, serum, preferably fetal calf serum (FCS), chondroitin-(4/6) sulfate, and fibroblasts, preferably at a concentration of approximately $1.5\times10^5$/mL. This mixture is gelled, for example, by increasing the temperature to room temperature, or 37° C., within approximately 2 min. After the gelling of the gels, it is preferred to add fibronectin to the gels. Fibronectin mediates the binding of the cells to macromolecules, for example, collagen, and the adhesion to neighboring cells. The subsequent culturing of the fibroblasts in the collagen gel preferably occurs in submerged culture; the latter term means that the cells are covered with a nutrient solution. The fibroblast-containing biomatrix is coated with cell culture medium and cultured at 37° C. and 5% $CO_2$ under standard conditions in a manner that is known in itself.

In an advantageous embodiment of the invention, the fibroblasts cultured in the biomatrix are redissolved out of the biomatrix, and optionally reintroduced into the biomatrix, in which the cells, after having been dissolved out, do not lose their specific metabolic capabilities and their differentiation status. The method according to the invention thus makes it possible to carry out an intermediate culturing of the fibroblasts in the biomatrix. With a reduced starting quantity of fibroblasts, the method according to the invention therefore offers the advantage that sufficient cell material can be made available for the production of dermis and/or skin equivalents.

An additional advantageous configuration of the invention provides that the function, morphology and/or differentiation status of the dermal fibroblasts introduced into an above-mentioned three-dimensional biomatrix are to be identified, cultured, and then and/or thereafter verified. The invention therefore also concerns screening and diagnostic methods carried out using dermal fibroblasts, in which the fibroblasts are cultured according to the above-mentioned methods and then and/or thereafter, for example, their pharmacological, ontological, toxicological, physiological, morphological and/or molecular biological parameters can be investigated. Besides the fibroblasts to be cultured, this biomatrix contains a framework made of a collagen solution of human or animal collagen, i.e., tissue-typical matrix proteins. According to the invention, the collagen-fibroblast gel is preferably subjected to a one- to two-day submerged culture.

In an additional advantageous embodiment of the invention, the dermal fibroblasts are cultured in the three-dimensional biomatrix as described above so that a dermis equivalent can subsequently be obtained. In connection with the present invention, "dermis equivalent" denotes a connective tissue-like layer made of collagen and fibroblasts that largely corresponds to native dermis. For this purpose—one to three days, preferably two days, after the above-described incubation of the gels, keratinocytes, stem cells of the skin or precursor cells of the keratinocytes—preferably precultured, undifferentiated keratinocyte stem cells, preferably from human biopsy tissue, are seeded on the gel, coated with KBM medium, and cultured for one to three days by submerged culturing. A complete differentiation of the keratinocyte layers is achieved by an airlift culture in approximately 1.8 mmol/L $CaCl_2$-containing KBM medium (without hEGF and BPE). In connection with the present invention, an "airlift culture" is a culture in which the height of the nutrient medium is precisely adjusted to the height of the biomatrix, while the keratinocytes or the cell layers formed by the keratinocytes lie beneath the nutrient level and are not covered by the nutrient medium; this means that culturing occurs at the air-nutrient medium boundary layer in which the supply for the cultures is provided from below. For this purpose, the inserts are transferred from the 24-well microtiter plate into the wells of a 6-well microtiter plate in which each well has a diameter of 3.5 cm. After a preferably 12-14-day, airlift culture, an in vitro whole skin model that is typical of the skin and consists of dermis and epidermis equivalents develops which can be used advantageously for the test methods according to the invention.

Then, keratinocytes or keratinocyte stem cells are seeded on the fibroblast-containing biomatrix. "Keratinocytes" denote cells of the epidermis that form the cornified pavement epithelium, or genetically altered keratinocytes, or their precursors, and may be of animal or human origin. Because the formation of a well differentiated epidermis with intact cornification is strongly dependent on the proportion of basal stem cells in the keratinocytes used, the keratinocytes seeded on the collagen gel are keratinocyte stem cells from human biopsy that are preferably as undifferentiated as possible, i.e., cytokeratin 19- or integrin β1-positive basal stem cells. The cells are preferably precultured cells, and particularly preferably keratinocytes in the first or second cell passage.

In a particularly preferred embodiment, it is preferred to use keratinocytes with a comparatively high proportion, for example 0.5%, 1%, 2%, 5%, 8% or 10% in the keratinocyte cell population, or comprising only undifferentiated stem cells. Using specific culture conditions—particularly submerged culturing for several days, and subsequently several days of air lift culture of the biomatrix—and specific culture media, the keratinocytes undergo differentiation to a multi-layered epidermal layer. Moreover, according to the invention, in a preferred embodiment, before, during or after the seeding of the keratinocytes, other cell types and/or other cells of other tissue types can also be seeded on the biomatrix, for example, immune system cells. It is advantageously achieved that the dermis equivalent is not subjected to an undefined shrinkage process for the duration of the culturing.

The invention therefore also concerns a skin-typical, three-dimensional, preferably human, in vitro skin equivalent, consisting of a dermis and an epidermis equivalent, and to a method for the production, culturing and use of this skin equivalent, as well as its components. Skin-typical whole skin models, which can also be called in vitro skin equivalents, can be used as test skin, particularly in dermatology and allergology, to study substances, for example potential drugs or cosmetics, or agents like light and heat, for their pharmacological effects, particularly their imitation, toxicity and inflammation effects, and for their tolerance.

An additional execution of the invention comprises the culturing of intestinal fibroblasts with the biomatrix obtainable according to the invention for the production of a three-dimensional human in vitro intestine test system, which preferably consists of Caco2 cells or intestinal epithelial cells. Intestinal fibroblasts are fibroblasts of animal or human origin or their precursor cells that occur in nature, particularly in the intestinal tissue, or that have been genetically altered. For the production of the intestinal fibroblast-containing biomatrix according to the invention, the collagen solution is treated and thoroughly mixed in the volume ratio 1:1 at 4° C. with a solution that is called gel solution, and preferably contains a two-fold concentrated cell culture medium, buffer, preferably Hepes buffer, serum, preferably 10% serum, and preferably $1.5 \times 10^5$/mL intestinal fibroblasts, particularly precultured intestinal fibroblasts. This mixture is gelled by increasing the temperature to room temperature or 37° [C]. The subsequent culturing of the intestinal fibroblasts in the collagen gel is preferably carried out in submerged culture. The fibroblast-containing biomatrix is incubated at 37° C.

An additional object of the invention is an in vitro test system that contains the biomatrix according to the invention and vital cells cultured in and/or on, the biomatrix. The invention particularly concerns in vitro systems that can be used for the analysis and diagnosis of infections and/or diseases of the human or animal body caused by pathogenic and/or parasitic microorganisms; in vitro test systems for the analysis and diagnosis of degenerated human and animal cells; in vitro test systems for the analysis and diagnosis of genetically altered human and animal cells, and in vitro test systems for the examination and testing of anti-infectives and antitumor drugs, particularly cytostatics, as well as three-dimensional animal in vitro organ and tissue models, particularly for tissues that are susceptible to infections like the intestine, liver, skin, cornea, trachea, and mucosa.

The cells to be investigated are preferably cultured in the three-dimensional, gel-like, connective tissue-like biomatrix according to the invention, and can multiply therein. This biomatrix contains the cells to be cultured in a collagen framework formed from a collagen solution, i.e., tissue-specific matrix proteins. Depending on the desired connective tissue, other additional cell types, preferably other primary cells, can be spread on the biomatrix. Using specific culture conditions and media, the cells preferably contained in the biomatrix, and the other cell types preferably spread on the biomatrix can undergo differentiation to a multilayered, three-dimensional, animal tissue or organ test model. Such cocultivation of the animal in vitro tissue or organ test system according to the invention with parasitic or pathogenic microorganism offers the possibility to study both the process of the infection and also the defense reaction of the corresponding organoid cell system. For example, larger quantities of an infected cell material and of the pathogen itself can be obtained. The material obtained can be further analyzed with the usual histological, biochemical, molecular-biological or immunological methods, for example, to study in greater detail releases of specific substances by the pathogen, like toxins or proteins relevant for resistance that occurs, or the release of specific substances by affected cells, like interleukins, as a defense reaction, or to prepare transcription and/or expression profiles on the basis of which, for example, virulence factors can be identified as targets for the development of anti-infectives.

A preferred execution of the invention also includes the coculturing of a three-dimensional, in vitro tissue and organ test system that has been produced according to the invention with pathogenic or parasitic microorganisms. In connection with the present invention, here the terms "pathogenic or parasitic microorganisms" also denote infectious agents, both eukaryotic and prokaryotic microorganisms, like bacteria, fungi, protozoa, viroids, but also prions or viruses which attack a macroorganism, particularly a human or animal organism, and live in or on tissues of this organism, and may lead to an infection of this organism, although this is not necessarily the case. In the context of the invention, the term "coculturing" denotes the simultaneous maintenance of the vital functions of animal cells and microorganisms, preferably in vitro, in the same environment that is appropriate for both, for example with the feeding and removal of metabolic educts and products, particularly also simultaneous multiplication of the cells and the microorganisms.

In an additional configuration of the invention, using an in vitro tissue and organ test system that has been produced according to the invention, particularly in connection with the coculturing method, the effect of chemical substances, particularly anti-infectives or agents on the infectious process, more specifically the growth of a pathogenic microorganism, is studied. In connection with the invention, the term "agent" particularly covers chemical, biological or physical means like light or heat that can have a potential effect on living cells.

A preferred execution of the invention comprises the analysis of degenerated cells. In connection with the invention, the term "degenerated" denotes any changes of a normal cell, for example cell polymorphism, anisocytosis, nuclear polymorphism, polychromasia, disturbed nucleus-plasma relationship, and aneuploidy, which can lead to a disturbed differentiation or dedifferentiation and deregulated cell growth and particularly concerns malignant tumor cells. From degenerated cells, particularly the above-mentioned tissues or organs, an in vitro tissue or organ test system is constructed, to acquire larger quantities of the degenerated cell material. The material obtained is further analyzed with the usual methods, for example histological, biochemical, molecular-biological or immunological methods, to investigate the distribution of specific substances, and to build transcription and expression profiles. From the in vitro tissue or organ test system that has been constructed from degenerated cells, the effect of drugs and substances that are potentially suitable as drugs is investigated, particularly with a view to their capacity to inhibit cell division.

In a preferred configuration of the invention, patient-specific degenerated cells are used to establish an in vitro tissue or organ test system to investigate the therapeutic possibilities for the specific patient's tumor disease.

A preferred configuration of the invention provides for the verification of genetically altered cells, particularly of the above-mentioned tissue and organs. In connection with the present invention, the term "genetically altered cells" denotes all the cells that have been manipulated with the help of genetic engineering methods, in which either foreign DNA and/or RNA was introduced into the cell, or the cell's own DNA and/or RNA was modified, for example by deletions, inversions or additions. In a particularly preferred embodiment, with a view to genetic therapy for patient-specific diseases, genetically altered cells are tested in vitro, particularly to determine their functionality, in which an in vitro tissue or organ test system is established using such genetically altered cells.

Finally, an additional object of the invention is the use of the collagen according to the invention for the production of a tissue equivalent or replacement, for the production of an organ equivalent or replacement, or for the production of an in vitro test system.

EMBODIMENT EXAMPLES

The invention is explained in greater detail by the following figures and examples, which should not be understood to be limiting.

FIG. 1 shows the histological representation of fibroblast cultures after 45 days in/on a biomatrix prepared according to the invention.

EXAMPLE 1

Isolation of Collagen from Collagen-containing Tissue

Isolation of the Collagen-containing Fibers

For the production of a collagen solution, tendons from rat tails are used as collagen-containing tissue. All the work was carried out under sterile conditions using sterile materials. The rat tails are surface disinfected with 70% alcohol after storage at −20° C. The skin of the rat tails is pulled off, and the individual collagen fibers are pulled out. When other starting tissues are used, any cells that might be present can be removed by mechanical, enzymatic or chemical treatment.

The collagen fibers are collected in phosphate buffered saline (PBS) (pH 7.2), surface disinfected for approximately 10 min in 70% alcohol, and then thoroughly washed with PBS. The weight of the fibers is determined.

Extraction of the Matrix Proteins

For the extraction of the matrix proteins, the fibers are transferred into a highly concentrated urea solution; the final concentration is 9 mol/L. This batch is stirred for approximately 24 h at approximately 4° C. The undissolved collagen portions are then removed by centrifugation (1000 rpm, 1 h, 8° C.). The collagen is now in solution and not in the form of a fiber, framework or matrix.

Gel Filtration

Alternatively to separation by centrifugation, the collagen solution in another batch is subjected to a gel filtration. For this purpose, after extraction, approximately 50 mL of the urea-containing collagen solution is applied to a 1.6-L column (diameter 6 cm, height 60 cm) with a packing corresponding to Superose™ 12 (GE Healthcare), and eluted at a throughput rate of approximately 25 mL/h. 100 fractions of 10 mL each are collected. Depending on the desired protein composition, several fractions are recombined, and others are discarded.

Gradient Dialysis

Gradient dialysis against water is carried out to remove the urea in the collagen solution. Starting at 9 mol/L urea, the dialysis is carried out in PBS for 7 days at 4° C. to 0 mol/L urea. In the process, the collagen is renatured to the greatest possible extent, as shown in corresponding analyses.

Lyophilization

In an additional batch, the urea-free collagen fraction obtained from dialysis is lyophilized in a known way to make it storable.

EXAMPLE 2

Characterization of the Isolated Matrix Proteins

The structure of the collagen proteins obtainable according to the invention was biophysically characterized, and are fractionated by gel filtration and freed of urea by gradient dialysis against water.

CD Spectroscopy

Circular dichroism spectroscopy (CD) is used for the verification of the protein structure. The characteristic spectra of so-called "triple helices" are obtained. They present a typical "signature," which is characterized by a small negative band between 217 and 227 nm and a possibly visible, less intense negative band near 200 nm. These spectra clearly differ from the CD spectra of collagen proteins with unordered structure ("random coil"), α helix or β-pleated sheet structures. The triple helix structure is typical for collagen 1, which predominates in the aqueous solution; most of the isolated collagen folds in water to the original native structure.

In an additional batch, collagen obtainable according to the invention is lyophilized and then redissolved in water, and processed by CD spectroscopy. It was found that the collagen solution prepared from lyophilized collagen also presents the characteristic triple helix structure. Lyophilized collagen prepared according to the invention presents a high water solubility without irreparably destroying the native structure of the collagen in the process. To date, this property has not been achieved with collagen from natural sources.

UV Spectroscopy

To confirm the CD results, UV spectra of the isolated collagen fraction were measured in the range from 190 to 320 nm. The UV spectra confirmed the analysis of the CD spectra.

There is an equilibrium between different protein structures. Thus it was found that, if the protein concentration is doubled, the characteristic peak of the spectrum is halved; the equilibrium shifts to the alternative conformation.

In a comparison experiment, an aqueous collagen solution obtainable by conventional acetic acid extraction was investigated. In contrast to the usual acetic acid extract, the collagen obtainable according to the invention presents characteristic amino acid residues in the UV spectrum. They primarily include histidine at a wavelength of 213 nm. This advantageously allows the direct determination of the concentration of the collagen obtainable according to the invention by means of objective spectroscopic and photometric methods.

Biochemical Characterization

In an additional batch, it was verified that the collagen obtainable according to the invention is glycosylated. By enzymatic digestion with O-glucanase any O-glycosylation present was cleaved. The protein obtainable in this way is then separated by two-dimensional gel electrophoresis and stained with Coomassie [blue]. Isoelectric focusing shows that, prior to the deglycosylation, the collagen obtainable according to the invention is localized in the pI range (isoelectric point) between 4.5 and 6. The theoretically expected value is 5.5. After deglycosylation, one obtains a characteristic "smear," which is a sign of the cleaved sugar. In spite of the deglycosylation, the isoelectric point of the proteins is maintained, and the molecular weight is accordingly reduced.

EXAMPLE 3

Production of a Biomatrix 16 mL of collagen solution are placed in 50-mL centrifuge tubes and put on ice. In each case, 600 µL are carefully poured into the well of a 24-well microtiter plate (diameter of each well 10 mm). As a result of a 2-min incubation at 37° C., gelling of the mixture occurs.

Before the seeding of cells to be cultured on it, the medium in the wells of the microtiter plate and from the gels, is first aspirated.

EXAMPLE 4

Production of a Fibroblast Culture

For the functional characterization of the biomatrix produced according to Example 3, fibroblasts were cultured on the matrix. As a comparison batch, matrices were used that had been produced by known methods (acetic acid extraction).

For the production of the fibroblasts, a method that is known in itself was used. In detail, human donor skin (foreskins) were incubated with Dispase solution and then treated with trypsin solution. The epidermal layer was pulled off the enzymatically pretreated tissue pieces, the dermis was then cut into small pieces with a scalpel and incubated for 30-45 min in collagenase type 4 (500 U/mL) at 37° C. Then the aspirated supernatant was centrifuged for 5 min at 1000 rpm. The pellets were resuspended in DMEM+10% FCS and recentrifuged. After aspirating the supernatant, the pellets were taken up in 2 mL DMEM+10% FCS and transferred to an uncoated cell culture flask. After culturing for one to two days, an additional 10-15 mL DMEM+10% FCS were added, and culturing was continued. Medium replacement was carried out every three days. The culturing was carried out in a water-vapor-saturated incubator under the usual cell culture conditions (37° C. and 5% $CO_2$ atmosphere).

In the comparison batch, the fibroblasts were passaged and taken up at a concentration of $1\times10^4$ cells/mL in a gel pouring solution (consisting of cell culture medium, serum and buffer), and pipetted into a collagen solution obtainable by acetic acid extraction. With the help of a pipette/syringe, the mixture was taken up and simultaneously mixed, and 500 µL each were pipetted in a 24-well plate. The gel was then incubated at 37° C. for 5 min in an incubator to allow the gels to gel. After gelling of the gels, they were mixed with approximately 1.5 mL/well DMEM+10% FCS+1% gentamicin, and cultured under standard cell culture conditions. After one week, considerable shrinkage of the cultures was observed in the comparison batch. After a culturing time of approximately 18 days, the experiments in the comparison batch had to be discontinued because of excessive shrinkage.

In contrast, in the batch according to the invention, the biomatrix obtainable according to the invention was first allowed to gel, and then the cells were introduced in gel pouring solution as a fibroblast suspension at a concentration of $1\times10^4$ cells/mL after passages. Then, they were cultured in a way that is known in itself (see comparison experiment). After more than 40 days of culturing time, vital staining confirmed that the fibroblasts had grown well. By means of microscopic observation and histological staining (hematoxylin-eosin) this growth could be observed and was made visible even after 60 days. The histological staining also showed that the fibroblasts have synthesized new matrix from the biomatrix (FIG. 1).

EXAMPLE 5

Production of a Multilayered In Vitro Skin Model

A skin model consisting of human fibroblasts and primary keratinocytes was produced.

The human fibroblasts were obtained as in Example 4. The production of the keratinocytes occurred as follows: The epidermis that had been dissolved from the enzymatically treated tissue pieces was subjected to an additional trypsin treatment and then mechanically triturated. The mechanically triturated epidermal particles were taken up in a special keratinocyte medium and/or stopped with trypsin inhibitor. The cells were then centrifuged at 1000 rpm for 5 min, the supernatant was discarded, and the pellets were carefully resuspended with 2 mL keratinocyte medium and transferred to a culture vessel. After approximately 4 h, medium replacement was carried out under sterile conditions. Medium replacement was then carried out every two days. The culturing occurred in a way that is known in itself under standard culture conditions (see Example 4).

For the production of the in vitro skin model, the collagen solution obtainable according to the invention (see Example 1) and a so-called gel pouring solution consisting of cell culture medium, serum, and buffer were prepared and put on ice. The fibroblasts were first passaged and taken up at a concentration of approximately $1\times10^4$ cells/mL in the gel pouring solution and immediately pipetted into the collagen solution without air bubbles. With the help of a pipette/syringe, the mixture was taken up and simultaneously mixed in the process. 500 µl each are pipetted into a 24-well plate with special insert (Nunc). The gels were then incubated at 37° C. for 5 min in an incubator. After gelling the gels, the latter were mixed with approximately 1.5 mL DMEM+10% FCS+1% gentamicin per well and incubated overnight at 37° C. The next day, the medium was aspirated. 25 mL fibronectin at a concentration of 50 µg/mg were now pipetted onto the gel, and the gel was replaced in the incubator for approximately 30 min.

Then the keratinocytes were seeded. For this purpose, the keratinocytes from the above-mentioned culture were passaged, and $1\times10^5$ cells/mL in 50 µL/KMBr+5% FCS was pipetted onto each of the gels. They were incubated for 20 min at 37° C. Subsequently, the gels were further cultured with KMBr+5% FCS in a submerged culture. In the subsequent five culture phases, the FCS concentration was reduced from 5% to 0%. They were then cultured further for 12-14 days in an environment exposed to air.

The invention claimed is:

1. A method for the isolation of collagen or collagen matrix proteins from collagen-containing tissue wherein the only extractant utilized is urea, comprising the steps:
    a) isolation of collagen-containing fibers from the tissues;
    b) incubation of the isolated collagen-containing fibers in an aqueous solution containing an extractant, in which the only extractant in the aqueous solution consists of urea in a final concentration of 5-15 mol/L, in which a collagen-containing fraction is dissolved out of the fibers;
    c) separation of the dissolved collagen-containing fraction from the fiber and tissue residue; and
    d) separation of the urea from the collagen-containing fraction and renaturing of the collagen by use of gradient dialysis in aqueous PBS, so that a collagen-containing aqueous solution with isolated collagen is obtained.

2. The method according to claim 1, in which the collagen-containing tissue is isolated rat tail tendons.

3. The method according to claim 1, in which the collagen-containing tissue is acellularized porcine small intestine.

4. The method according to claim 1, in which, in step b) the final urea concentration is 7-12 mol/L.

5. The method according to claim 1, in which, in step b) the final urea concentration is 9 mol/L.

6. The method according to claim 1, in which, in step b) the collagen-containing fibers are stirred with the urea solution.

7. The method according to claim 1, in which, in step b) the collagen-containing fibers are incubated with the urea solution for 12-36 h.

8. The method according to claim 1, in which, in step c) the separation of the dissolved collagen-containing fraction is carried out by centrifugation and/or filtration.

9. The method according to claim 1, in which, in step c) the separation of the dissolved collagen-containing fraction occurs by fractionation using gel filtration, and optionally subsequently recombining several fractions.

10. The method according to claim 1, in which, in step d) the dialysis is carried out against water in the cold for 4-12 days.

11. The method according to claim 1, in which the aqueous collagen solution obtained has a collagen content of 3-8 mg/mL.

12. The method according to claim 1, in which, in an additional step the collagen solution obtained is lyophilized.

13. The method according to claim 1, in which the collagen content of the aqueous collagen solution obtained is determined by UV spectroscopy (UV).

14. The method according to claim 13, in which, for the concentration determination in the UV spectrogram, the characteristic amino acid signature of histidine at 213 nm is evaluated.

15. Method for the production of a biomatrix, comprising the steps:
    performance of the steps a) to d) of the method according to claim 1;
    e) mixing of the collagen solution obtained with cell culture medium in a ratio from 2:1 to 1:2 to make a collagen-containing matrix precursor solution, and
    f) gelling of the matrix precursor solution to a collagen-containing biomatrix at increased temperature.

* * * * *